(12) United States Patent
Speer et al.

(10) Patent No.: US 7,713,715 B2
(45) Date of Patent: May 11, 2010

(54) METHOD FOR DIAGNOSING INFECTIONS

(75) Inventors: Clarence A. Speer, Louisville, TN (US); Shigetoshi Eda, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 96 days.

(21) Appl. No.: 11/220,156

(22) Filed: Sep. 6, 2005

(65) Prior Publication Data

US 2007/0054334 A1 Mar. 8, 2007

(51) Int. Cl.
*G01N 33/554* (2006.01)
*G01N 33/569* (2006.01)
*G01N 33/53* (2006.01)

(52) U.S. Cl. ................ 435/7.32; 435/7.31; 435/7.1

(58) Field of Classification Search ............... 435/7.32, 435/7.3; 424/9.1, 234.1
See application file for complete search history.

(56) References Cited

U.S. PATENT DOCUMENTS 6,926,898 B2 8/2005 Rosen
2002/0064801 A1* 5/2002 Ryan et al. ............... 435/7.3

OTHER PUBLICATIONS

Vannuffel et al., Development of Species-specific Enzyme-Linked Immunosorbent Assays for Diagnosis of Johne's Disease in Cattle. Journal of Clinical Microbiology, vol. 32, No. 5, pp. 12-111216, May 1994.*
Vannuffel et al., Occurrence, in Crohn's Disease, of Antibodies Directed against a Species-specific Recombinant Polypeptide of Mycobacterium paratuberculosis Clinical and Diagnostic Laboratory Immunology, vol. 1, No. 2, pp. 241-243, Mar. 1994.*
Cocito et al., Paratuberculosis Clinical Microbiology Reviews, vol. 7, No. 3, pp. 328-345, Jul. 1994.*
Kesel et al. ,journal of Clinical Microbiology, vol. 3, No. 4, pp. 947-954, Apr. 1993.*
De Kesel et al. ,Scandinavian Journal of Immunology, vol. 36, No. 2, pp. 201-212, 1992.*
Waters et al. ,Infection and Immunity vol. 67, No. 4, pp. 1593-1598, Apr. 1999.*
Cruse et al. ,The Illustrated Dictionary of Immunology, second edition 2003, p. 224 and p. 553.*
Waters et al. (Infection and Immunity vol. 67, No. 4, pp. 1593-1598, Apr. 1999).*
Burgess et al. (J of Cell Biology, 1990 vol. 111, pp. 2129 2138).*
Bannantine et al. (Microbiology, vol. 149, pp. 2061-2069, 2003).*
Whitlock, RH, et al, ELISA and fecal culture for paratuberculosis (Johne's disease): sensitivity and specificity of each method, Veterinary Microbiology, 77:387-398 (2000).
Fang, Y, et al, Comparison of Real-Time, Quantitative PCR with Molecular Beacons to Nested PCR and Culture Methods for Detection of *Mycobacterium avium* subsp. *paratuberulosis* in Bovine Fecal Samples, J. Clin. Microbiology, 40(1):287-291 (2002).
Collins, DM, et al, "Comparison of polymerase chain reaction tests and faecal culture for detecting *Mycobacterium paratuberulosis* in bovine faeces", Veterinary Microbiology, 36:289-299 (1993).
Vary, PH, et al, "Use of Highly Specific DNA Probes and the Polymerase Chain Reaction to Detect *Mycobacterium paratuberulosis* in Johne's Disease", J. Clin. Microbiology, 28(5):933-937 (1990).
Sweeney, RW, et al, "*Mycobacterium paratuberulosis* isolated from fetuses of infected cows not manifesting signs of the disease", Am. J. Vet. Res., 53(4):477-480 (1992).
Klausen, J, et al, "Evaluation of serum and milk ELISAs for paratuberculosis in Danish dairy cattle", Preventive Veterinary Medicine, 58:171-178 (2003).
Zeus Scientific, "FTA-ABS Double Stain IFA Test", Brochure on web page www.zeussci.com/docs/r2190 (1997).
Zeus Scientific, "Toxoplasma IFA Test System", Brochure on web page www.zeussci.com/docs/r2360 (1998).
Zeus Scientific, "FTA-ABS IFA Test System", Brochure on web page www.zeussci.com/docs/r2180 (1997).
Zeus Scientific, "Mycoplasma Pneumoniae Antibody (MP) IgG Test", Brochure on web page www.zeussci.com/docs/r2270 (1997).
Zeus Scientific, "Legionella DFA Test System", Brochure on web page www.zeussci.com/docs/r2075 (1998).
Peng, Z, et al, "Highly sensitive and specific ELISA with monoclonal antibody capture to measure *Dermatophagoides farinae* 1-specific IgE", Annals of Allergy, Asthma, & Immunology, 80:274-278 (1998).
Panbio, "Coxiella Burnetii (Q Fever) IgG ELISA Test", Cat No. E-QFB01G, (2002).
OIE World Organisation for Animal Health, "Manual of Diagnostic Tests and Vaccines for Terrestrial Animals", Chapter 2.2.11 "Leishmaniosis" (Jul. 23, 2004).

* cited by examiner

*Primary Examiner*—Robert Mondesi
*Assistant Examiner*—Khatol Shahnan-Shah
(74) *Attorney, Agent, or Firm*—Howard Eisenberg, Esq.

(57) ABSTRACT

Antigens are removed from the surface of an organism, such as a microorganism, without disrupting the organism and releasing internal antigens of the organism. The free surface antigens of the organism may be used to determine the presence of infection in an animal due to the organism by determining the presence of antibodies that bind to the free surface antigens in a sample obtained from the animal.

22 Claims, 4 Drawing Sheets

| Group # | Fecal culture test | Intact MAP | MAP Surface Antigens | Group # | Fecal Culture Test | Intact MAP | MAP Surface Antigens |
|---|---|---|---|---|---|---|---|
| I | Negative | (0.07) | 0.01 | II | Negative | 0.14 | 0.59 |
| I | Negative | 0.12 | 0.53 | II | Negative | 0.12 | 1.32 |
| I | Negative | 0.14 | (0.12) | II | Negative | 0.33 | 0.71 |
| I | Negative | 0.01 | 0.00 | II | Negative | 0.05 | 0.66 |
| I | Negative | (0.10) | (0.24) | II | Negative | 0.34 | 0.85 |
| I | Negative | 0.07 | 0.04 | II | Negative | 0.73 | 0.54 |
| I | Negative | (0.08) | 0.02 | II | Negative | (0.18) | 0.63 |
| I | Negative | (0.04) | 0.00 | II | Negative | 0.84 | 0.74 |
| I | Negative | 0.11 | 0.06 | II | Negative | 0.25 | 0.39 |
| I | Negative | 0.11 | 0.10 | II | Negative | 0.47 | 0.86 |
| I | Negative | (0.02) | (0.18) | II | Negative | 0.32 | 0.68 |
| I | Negative | (0.10) | (0.04) | II | Negative | 0.30 | 0.53 |
| I | Negative | 0.01 | (0.11) | II | Negative | 0.09 | 0.69 |
| I | Negative | 0.05 | 0.07 | II | Negative | 0.26 | 1.85 |
| I | Negative | 0.09 | (0.02) | II | Negative | 0.30 | 0.54 |
| I | Negative | 0.10 | 0.09 | II | Negative | 0.32 | 0.40 |
| I | Negative | 0.02 | 0.15 | II | Negative | 0.31 | 0.52 |
| I | Negative | (0.06) | (0.25) | II | Negative | 0.40 | 0.82 |
| I | Negative | 0.01 | (0.06) | II | Negative | 0.24 | 0.67 |
| I | Negative | 0.30 | 0.54 | II | Negative | 0.50 | 0.79 |
| I | Negative | 0.13 | 0.31 | II | Negative | 0.37 | 0.72 |
| I | Negative | 0.16 | 0.27 | II | Negative | 0.27 | 0.80 |
| I | Negative | (0.09) | (0.26) | II | Negative | 0.17 | 0.20 |
| I | Negative | (0.02) | (0.10) | II | Negative | 0.18 | 0.96 |
| I | Negative | 0.19 | 0.14 | II | Negative | 0.25 | 0.35 |
| I | Negative | (0.06) | (0.22) | II | Negative | 0.31 | 0.54 |
| I | Negative | (0.05) | (0.22) | II | Negative | 0.27 | 0.69 |
| I | Negative | (0.04) | (0.22) | II | Negative | 0.30 | 0.82 |
| I | Negative | 0.01 | (0.19) | II | Negative | 0.57 | 0.77 |
| I | Negative | 0.13 | 0.39 | III | 1,0,0,0 | 0.18 | 0.48 |
| II | Negative | 0.28 | 0.54 | III | 1,0,0,0 | 0.51 | 0.50 |
| II | Negative | 0.27 | 1.08 | III | 1,0,0,0 | 0.43 | 0.72 |
| II | Negative | 0.43 | 1.16 | III | 1,0,0,0 | 0.22 | 1.14 |
| II | Negative | (0.05) | 1.24 | III | 1,0,-,- | 0.37 | 1.74 |
| II | Negative | 0.27 | 0.65 | III | 2,0,0,0 | 0.16 | 0.69 |
| II | Negative | 0.31 | 0.43 | III | 1,2,0,0 | 0.46 | 0.88 |
| II | Negative | 0.22 | 1.13 | III | 1,1,1,1 | 0.28 | 0.70 |
| II | Negative | 0.24 | 1.01 | III | 3,1,0,0 | 0.39 | 0.35 |
| II | Negative | 0.31 | 1.31 | III | 2,1,2,0 | 0.34 | 0.76 |
| II | Negative | 0.18 | 1.09 | III | 1,2,2,3 | 0.22 | 1.36 |
| II | Negative | 0.45 | 1.37 | III | 1,3,3,1 | 0.33 | 0.43 |
| II | Negative | 0.34 | 0.31 | III | 3,1,1,4 | 0.40 | 0.63 |
| II | Negative | 0.11 | 0.60 | III | 3,1,6,1 | 0.25 | 0.62 |
| II | Negative | 0.17 | 0.76 | III | 4,1,3,7 | 0.44 | 0.61 |
| II | Negative | 0.44 | 0.95 | III | 3,4,5,5 | 0.51 | 0.73 |
| II | Negative | 0.28 | 0.78 | III | 7,7,5,4 | 0.44 | 0.84 |
| II | Negative | 0.18 | 0.84 | III | 4,9,8,22 | 1.03 | 1.11 |
| II | Negative | 0.27 | 1.09 | III | 17,13,14,- | 0.29 | 0.64 |
| II | Negative | (0.11) | 0.88 | III | 3x TNTC | 0.67 | 0.18 |
| II | Negative | 0.28 | 1.23 | III | 4xTNTC | 1.12 | 0.64 |
| II | Negative | 0.33 | 0.63 | III | 4xTNTC | 0.69 | 0.54 |
| II | Negative | 0.06 | 0.56 | III | 4x TNTC | 0.46 | 0.37 |
| II | Negative | 0.22 | 0.48 | | | | |

Fig. 8

METHOD FOR DIAGNOSING INFECTIONS

FIELD OF THE INVENTION

The invention pertains to the field of diagnosing infection due to an organism, such as a microbial organism.

BACKGROUND OF THE INVENTION

Perhaps the most important aspect in diagnosing the cause of symptoms experienced by a patient when an infectious agent is suspected as being the cause of the symptoms is the establishment of the identity of the specific organism that is etiologically responsible for the symptoms. Additionally, a significant need exists for a method to identify people and animals that have been infected with an organism, such as a microorganism, including people and animals who are not exhibiting signs or symptoms of disease associated with the organism.

Classically, the presence of infection due to a particular infectious microorganism has been established by isolating the organism from the body of a patient, culturing the organism on a suitable culture medium, and identifying the cultured organism based on biochemical, immunological, or other tests. This method suffers from several disadvantages. Diagnosis by culture and identification often requires a substantial period of time when growing organisms that have a slow growth rate. For example, standard culture and identification methods for *Mycobacterium avium* subsp. *paratuberculosis*, the causative organism of Johne's disease in cattle and Crohn's disease in people, may require 8 to 16 weeks or more to perform due to the very slow growth rate of this organism. Another disadvantage to culture and identification methods of diagnosis is that the particular organism causing disease in a patient may fail to grow on standard culture media, leading to a negative culture result and a failure in diagnosis. Additionally, because such methods require the isolation of an infectious organism from a patient, these methods are inappropriate at times when the patient is not shedding the organism or if the organism is located in an inaccessible location within the body of the patient.

In recent years, molecular biological and immunological methods have been developed for the diagnosis of infectious diseases. These methods generally fall into three categories, detection of genome nucleic acids, detection of protein, and detection of antibodies directed against a pathogen.

Diagnosis by identification of genome nucleic acids is typically performed using either or both amplification of DNA by polymerase chain reaction (PCR) followed by identification of PCR fragments produced or by use of probes that bind specifically to a portion of the genome of a suspected causative organism. These methods, especially when used in combination, can be very sensitive and specific methods to establish a diagnosis of a causative organism. There are several disadvantages associated with these methods. They are expensive, require sophisticated technical expertise to perform, and generally take several days to obtain enough microorganisms for a diagnosis. Another significant disadvantage associated with diagnosis by detection of genome nucleic acids is that an organism must be isolated in order to obtain the genome nucleic acids.

Diagnosis by identification of proteins is typically performed by an enzyme-linked immunosorbent assay (ELISA). In this test, an antigen from a microorganism, typically a disrupted microorganism or a portion of a microorganism, is bound to a solid support and reacted with a first antibody in a test sample, typically serum, that is specific for the antigen of interest. A labeled second antibody that binds to antibodies in test serum is then exposed to the solid support complex to provide a means for identification of the presence of the antigen. ELISA tests, however, suffer from several disadvantages including low sensitivity and the requirement to provide two different antibodies for the detection of an antigen. ELISA testing requires skilled laboratory technicians and can provide false results if samples contain cross-reacting antibodies.

An example of an infectious disease for which currently available diagnostic methods are inadequate is Johne's disease, a disease in cattle caused by *Mycobacterium avium* subsp. *paratuberculosis* (MAP). Johne's disease results in decreased milk production and early culling of infected cows resulting in an annual loss of approximately $1.5 billion to the agricultural industry in the United States. Considerable evidence exists that MAP is also the causative organism of Crohn's disease in humans. Despite this significant impact on the U.S. economy and on human health, there is no effective diagnostic test to determine early infections by MAP.

At present, fecal culture is considered to be the most accurate means of diagnosing MAP infection. However, this diagnostic test has low sensitivity (less than 50%) and is capable of detecting infections only in animals that are actively shedding MAP in their feces. Additionally, diagnosis of MAP by culture typically requires 8 to 16 weeks for growth of the organism.

Other diagnostic tests for Johne's disease include PCR, complement fixation, agar gel immunodiffusion, and ELISA. These tests, each of which utilizes a molecular extract of MAP, have inherently low specificity or sensitivity for MAP and suffer from the disadvantages present with these methods as indicated above.

A significant need exists for a diagnostic method to detect infection by an organism, such as a microorganism, that can be performed rapidly, is highly sensitive, is highly specific, and which may be performed by an individual lacking sophisticated laboratory training. Particularly, a significant need exists for such a diagnostic method that is useful for diagnosing diseases such as those caused by MAP.

BRIEF DESCRIPTION OF THE DRAWINGS

FIG. 8 is a chart showing results of testing 3 groups of cows for infection with MAP. Group I (n=30) were cows that tested negative for Johne's disease by fecal culture, conventional ELISA, and gamma interferon. Group II (n=52) were cows that tested negative for Johne's disease by fecal culture and conventional ELISA, but developed clinical signs of Johne's disease. Group III (n=23) were cows that tested by multiple fecal cultures and were found to be positive for Johne's disease on at least one of the fecal culture tests. In the column headed "Fecal Culture Tests", "negative" means that no MAP cultures were identified on any fecal culture test from that particular cow, numbers indicate the number of colonies that were found on serial tests. In the columns headed "Intact MAP" and "MAP Surface Antigens", numbers indicate optical density. Test values of 0.23 or higher under "Intact MAP" indicate a positive test. Test values of 0.35 or higher under "MAP Surface Antigens" indicate a positive test. Test values indicating a positive test for MAP are in shaded boxes. Numbers in parentheses indicate a negative value. 3×TNTC and 4×TNTC indicate that the fecal culture test was conducted 3 or 4 times and that the numbers of colonies were too numerous to count.

DESCRIPTION OF THE INVENTION

Figure 1:
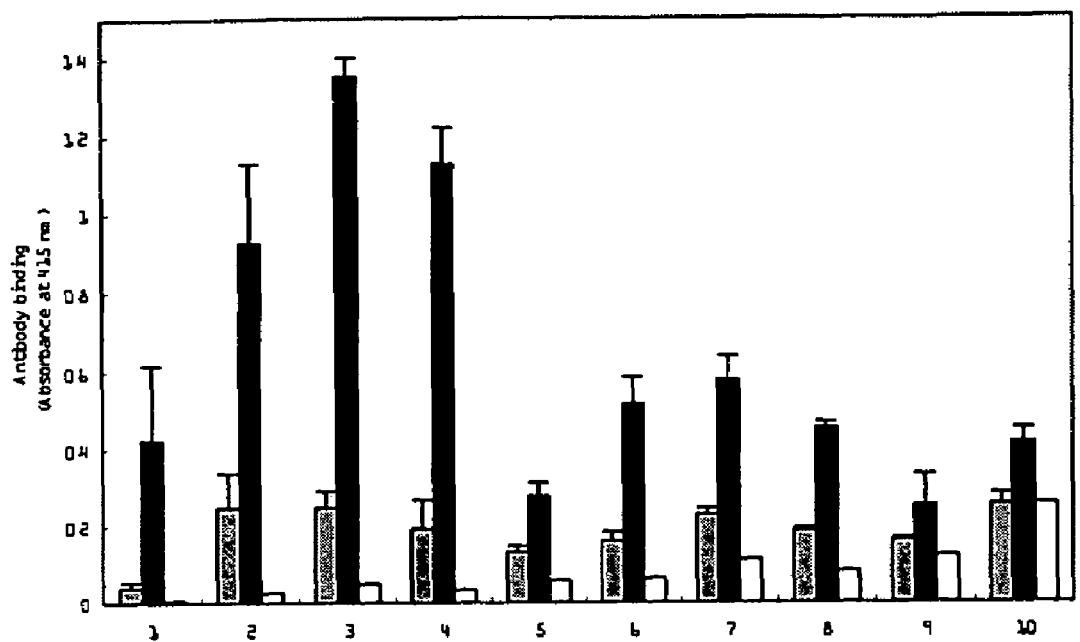
FIG. 1 is a bar graph showing antibody binding to free surface antigens extracted according to the invention with various solvents. The solvents shown are 1-distilled water, 2-methanol, 3-ethanol, 4-propanol, 5-acetonitrile, 6-acetone, 7-methylene chloride, 8-chloroform, 9-ether, and 10-hexane. The shaded bars represent serum from cattle known to be free of MAP infection. The black bars represent serum from cattle known to be infected with MAP. The open bars represent samples containing dilution buffer only and no serum. Optical density was determined on wet well containing the various samples.

It has been unexpectedly discovered that increased accuracy of diagnosis of infection, such as evidenced by increased specificity and sensitivity, can be obtained by utilizing a multiplicity of free surface antigens from an organism, such as a microorganism, as a test antigen to determine the presence of an infection in an animal due to that particular organism.

In this specification, the term "free surface antigen" refers to an antigen that is normally found on the surface of an organism, such as a microorganism, but which has either been removed from the surface of the organism or has been synthetically produced, for example by recombinant means.

The invention is described in detail herein with reference primarily to microbial infections, such as bacterial infections exemplified by mycobacterial infections, and particularly with reference to *Mycobacterium avium*, and most particularly with reference to *Mycobacterium avium* subsp. *paratuberculosis* (MAP), the causative organism of Johne's disease in cattle and Crohn's disease in humans. This organism has proven to be a very difficult organism to establish as the cause of disease symptoms in cattle and in people and presents, therefore, a significant test to establish the efficacy, specificity, and sensitivity of the method of the present invention. It is to be understood, however, that MAP is merely an illustrative example and that the method of the invention is applicable to infection due to any organism, as specified below.

In one embodiment, the invention is a method for obtaining free surface antigens from an organism, such as a microorganism. According to this embodiment of the invention, an organism is maintained in suspension in a fluid containing a chemical extraction agent, antigens from the surface of the organism are caused to be removed from the organism and to be in suspension or solution within the fluid, and the free surface antigens in the fluid are separated from the portions of the organism other than the free surface antigens.

Preferably, in accordance with this embodiment of the invention, the integrity of the organism is not destroyed during the process by which surface antigens are removed from the surface of the organism. That is, it is preferred that the only antigens that are removed from the organisms are those that are normally present on the surface of the organism and that the organism remains intact, other than having lost antigens from its surface.

In accordance with the invention, an organism, such as a microorganism, is suspended in a liquid in which surface antigens will be removed from the organism. If the organism was grown on a solid culture medium, one or more colonies of the organism may be placed within a suspension fluid containing an extraction agent. If the organism was grown or maintained in a liquid culture medium, it is preferable to remove the organism from the culture medium, such as by centrifugation to produce a pellet containing the organism, and to resuspend the pelleted organism in a suspension containing the extraction agent. Following the removal of surface antigens from the organism, the free surface antigens are isolated, such as by centrifugation with retention of the supernatant or by filtration with retention of the filtrate fluid.

The extraction agent that is suitable for the method of the invention is a chemical compound that can be used to remove antigens from the surface of an organism. Polar antigens, such as carbohydrates, polypeptides, and polar lipids, may be extracted by extraction agents such as alcohols and aldehydes. Apolar antigens, such as most lipids, may be extracted by extraction agents such as acetone, chloroform, and hexanes. If desired, mixtures of extraction agents, such as mixtures of extraction agents for polar and for apolar antigens, may be used. An example of such a mixture is chloroform and methanol.

The surface antigens may be removed from the surface of the organism by any method by which such removal may be realized. For example, removal may be by mechanical treatment of the organism. Examples of mechanical treatment methods include sonication, vortexing, or French and Ribi presses.

Surface antigens may be removed by chemically treating the organism. Examples of chemical agents that may be used to remove antigens from the surface of a microorganism include phenol, methanol, chloroform, isopropyl alcohol, ethanol, tertiary butyrol, ether, detergents such as TWEEN™ 20 or TWEEN™ 80, sodium dodecyl sulfate, and acid or alkaline treatment.

Preferably, the surface antigens are removed by mechanical treatment of the organism, and most preferably by mechanical treatment of the organism combined with treatment of the organism with an extraction agent. Mechanical methods are capable of being modulated so that antigens are removed from the surface of an organism without disrupting the integrity of the organism itself. Although such removal of surface antigens with keeping the organism intact is possible by using chemical agents alone, it is conceived to be more difficult to accomplish this without disrupting the integrity of the organism, that is without releasing from the organism antigens that are normally located within the organism and are not exposed on the organism's surface.

The removal of antigens from the surface of an organism without disrupting the organism and removing internal antigens from the organism is referred to herein as "gentle dislodgement" of surface antigens. It is conceived that such gentle dislodgement is an essential component of the method of this embodiment of the invention.

The organism of the invention may be any infective organism that has one or more antigens on its surface that may be removed from the organism without disrupting the organism itself. Examples of microorganisms suitable for the invention include bacteria, fungi, protozoans, rickettsia, and chlamydia. The organism suitable for the invention may also be a multicellular endoparasite, typically a helminth. Because many viruses produce surface antigens that are derived from a host organism, it is conceived that the method of the invention is not applicable to viruses and, therefore, viruses are specifically excluded from the scope of the invention.

Examples of specific microorganisms from which surface antigens may be obtained by the method of the invention include but are not limited to *Campylobacter, Actinomyces, Streptococcus, Staphylococcus, Salmonella, Chlamydia, Listeria, Borrelia, Pasteurella, Yersinia, Brucella, Leptospira, Listeria, Shigella, Mycobacterium, Haemophilus, Bordatella, Legionella, Escherichia coli, Actinobacillus, Clostridium, Helicobacter, Eimeria, Toxoplasma, Sacrocystis, Neospora, Cryptosporidium, Cyclospora, Trypanosoma, Plasmodium, Babesia, Theileria, Entamoeba, Acanthomoeba, Naegleria*, and *Candida*.

Examples of helminths from which surface antigens may be obtained by the method of the invention include but are not limited to *Ostertagia, Trichostrongylus, Haemonchus, Cooperia, Nematodirus, Oesophagostomum, Dirofilaria, Ascaris, Toxacara, Trichuris, Necator, Ancylostoma, Enterobius, Schistosoma*, and various flukes.

In accordance with a preferred embodiment of the method of the invention for obtaining surface antigens from an organism, an organism, such as a microorganism, is suspended in a fluid that contains an extracting agent, such as formaldehyde with or without methanol or such as ethanol, and the suspension is then agitated, such as by sonication or vortexing, at an intensity and for a time sufficient to gently dislodge surface antigens from the organism. Sonication is preferably applied as a brief burst, such as between about a half second to less than 10 seconds, preferably less than five seconds, and most preferably about two-seconds, or by vortex swirling. For vortex swirling, because it is less forceful than sonication, longer treatment times may be employed without the risk of destroying the integrity of the organism. Thus, vortex treatment times ranging from one to two seconds up to several minutes or more may be employed for gentle dislodgement of surface antigens. Following the gentle dislodgement, free surface antigens are then removed from the fluid, such as by centrifugation with retention of the supernatant or by filtering with retention of the liquid filtrate to remove particulate matter.

A test for determining that surface antigens have been gently dislodged from an organism in accordance with the invention may be based upon the degree of reactivity of the product obtained by the process of removing surface antigens described above. Specifically, one may determine whether the amount of mechanical or chemical treatment of an organism is sufficient or is too much by determining the degree of binding of a standard sample known to contain antibodies to one or more surface antigens of the organism of interest. In this way, a curve is obtained that permits one skilled in the art to optimize the treatment of an organism in order to obtain surface antigens to be used in diagnosis.

Optimal treatment of an organism to remove surface antigens from the organism will result in maximal binding of antibodies present in a fluid contacted with the free surface antigens. If an organism is treated to a degree in which surface antigens are not removed at all from the organism, then contacting the product of the treatment to a test fluid known to contain antibodies to the organism will show minimal or no binding. If the organism is treated to a degree in which surface antigens are removed from the organism, but to a degree below that which is optimal, then reduced binding of surface antigens to antibodies in the test fluid will be observed. On the other hand, if the organism is treated to a degree in which surface antigens are removed but such treatment is continued so that the organism is disrupted, resulting in the release of internal microbial antigens, then binding of antibodies in the test fluid to free surface antigens will also be below optimal. Preferably, one may perform such test, such as by using increasing times of sonication or vortexing, to obtain graphic data that will indicate the amount of treatment that will provide the optimal amount of binding of antibodies in a test fluid with free surface antigens from the organism.

In another embodiment, the invention is a method for diagnosing an infection in an animal caused by an organism, such as a microorganism. The diagnostic method of the invention is a based on the binding of one or more antibodies in a fluid obtained from an animal to one or more specific antibody binding sites that exist or existed on the surface of a particular infective organism. In accordance with this method, a test sample, preferably a fluid sample, is obtained from an animal suspected of being infected with an organism. The test sample is exposed to a free surface antigens of the organism, such as free surface antigens that have been obtained by the above-described method of the invention for obtaining free surface antigens from an organism, for a time sufficient to permit an antibody in the test sample that binds to an antibody binding site on a surface antigen of the organism to bind to the antibody binding site. It is then determined if the test sample contains an antibody that binds to the free surface antigens. The test is positive for infection with the organism if antibodies in the test sample are found to bind to the free surface antigens of the organism, such as by determining the presence of antibody/surface antigen conjugates.

In one preferred embodiment, the test sample is exposed to free surface antigens of a multiplicity of different organisms, such as different microorganisms. In this way, the method of the invention may be used as a screening test for infection due to an array of organisms. This type of screening test is particularly useful for evaluating the presence of infections in animals that are to be shipped, especially in situations such as the transportation of an animal from an area in which certain diseases are known to be prevalent to an area in which such diseases are not found. If the test is positive for infection, further tests may then be performed to determine the specific organism with which the subject is infected.

The method of the invention is distinct from presently utilized methods for diagnosis of microbial infection and provides several advantages that are unobtainable from such methods. For example, the method of the invention may be performed rapidly. In a field version of the method of the invention, a positive or negative test result may be obtained rapidly, typically within about two hours, in contrast to culture method that require days or weeks. The method of the invention is extremely sensitive, more sensitive than presently available methods. Unlike culture methods, the method of the invention does not require isolation of an organism from an infected animal or the need to culture an organism in vitro. The method of the invention can be used to provide a positive diagnosis even during periods when an infective pathogen is not detectable in, or isolatable from, a host animal. Additionally, the method of the invention has a specificity that is higher than is obtained with other presently available methods of diagnosis.

Unlike recent innovations in diagnosis such as those based on nucleic acid or protein identification, the method of the invention is not based on the determination of the presence in an infected animal of any specific macromolecule peculiar to a particular organism. Also, unlike presently available tests based on antibody binding, such as ELISA testing, the method of the invention does not present an external antibody to determine if it binds to an extract of an organism or portion of an organism that is present in a host animal. Rather, the method of the invention is based upon determining that one or more antibodies present in a test sample isolated from the body of a host animal binds to antigens obtained from a particular organism and which antigens are brought into contact with the test sample.

In comparison with presently available ELISA testing in which fluid, such as serum, from an animal is contacted with bound antigens obtained by disrupting a microorganism and thereby releasing both surface and internal microbial antigens, the diagnostic method of the invention provides a more accurate diagnosis of infection due to a particular organism. Such increase in accuracy of diagnosis may be based, for example, on measurements of sensitivity and specificity.

Thus, the method of the invention provides several additional advantages previously unobtainable by present diagnostic methods. The method of the invention may be performed rapidly. In a field version of the method of the invention, a positive or negative test result may be obtained rapidly, typically within about two hours. The method of the invention is extremely sensitive, more sensitive than presently available methods. The method of the invention can be used to provide a positive diagnosis even during periods when a microbial pathogen is not detectable in, or isolatable from, a host animal. Additionally, the method of the invention has a specificity that is higher than is obtained with other presently available methods of diagnosis.

The method of the invention is useful for the diagnosis of infections in animals. Such animals include mammals, such as humans and non-human primates, carnivores such as dogs, cats, bears, and weasels, ungulate ruminants and non-ruminants such as horses, cattle, goats, sheep, and pigs, non-ungulate ruminants such as camels and llamas, pinnipedia such as seals and sea lions, lagomorpha such as rabbits and hares, rodentia such as squirrels, rats, and mice, cetacea such as whales, dolphins, and porpoises, and proboscidea such as elephants. Such animals also include non-mammalian vertebrates such as birds, reptiles, amphibians, and fish.

A suitable test sample that is obtained from an animal in accordance with the method of the invention may be any fluid or tissue in which an antibody that specifically binds to a suspected causative organism would likely be present if the animal were infected with that organism. Typically, the test sample is blood or a portion thereof, such as plasma or preferably serum. However, it is contemplated that other sample sources may be utilized in accordance with the invention. The selection of such source of test sample will vary depending, primarily, on the symptoms and signs of an infected animal and the suspected cause of such symptoms or signs. Thus, the test sample may be obtained from fluids such as saliva, milk, pus, tears and other ocular discharges, nasal discharges, sputum, cerebrospinal fluid, peritoneal or pleural fluid, urine, feces, and vaginal, uterine, or urethral secretions and discharges. Fluids may also include those that are produced as part of a pathologic process such as exudates or transudates, such as from the skin, the pleural or peritoneal cavity, the oral cavity, or from the digestive, respiratory, or genital system. The test sample may also be a solid tissue sample if appropriate for diagnosis of a particular disease.

The test sample may be obtained by whatever method is appropriate to obtain such a sample. Thus, the test sample may be obtained by methods such as syringe withdrawal of fluid, including vascular puncture, such as by venipuncture, or by withdrawal of fluid from other sources as described above, or by biopsy.

The organism that is diagnosed by the method of the invention is any organism, such as a microorganism, that is capable of eliciting an antibody response in an animal infected by such organism and from which organism surface antigens may be extracted without disruption of the organism and consequent release of internal, non-surface antigens. Thus, infective microorganisms that may be diagnosed by the method of the invention include bacteria, fungi, protozoa, rickettsia, and chlamydia. Infective multicellular organisms that may be diagnosed by the method of the invention include helminths.

The test sample may be exposed to free surface antigens of an organism, such as a microorganism, preferably free surface antigens that have been gently dislodged from an organism, in any way that permits antibodies that are contained in the test sample to interact with the free surface antigens. Thus, in a preferred embodiment, the test sample and the free surface antigens are combined in a vessel such as a test tube or a well and are mixed together, such as by stirring, vibrating, oscillating, or tapping the test tube or well. The test sample and the free surface antigens may also be reacted together on a surface such as on a slide, filter, or membrane, such as a nitrocellulose membrane.

In accordance with the method of the invention, the test sample is exposed to a population of free surface antigens, such as those that have been gently dislodged from an organism, for example by sonication, preferably performed while the organism is in suspension in a fluid containing an extraction agent. Such free surface antigens preferably contain a multiplicity of antigenic binding sites that are presented to the antibodies in a test sample. It has been unexpectedly discovered that such free surface antigens, such as those that have been obtained by gently dislodging from an organism, such as by sonication or vortexing at a level that dislodges antigens from the surface of an organism but does not disrupt the organism so as to release internal antigens, provides the optimum availability of binding sites for binding to antibodies in a test sample.

If desired, prior to gentle dislodgement of surface antigens, the organisms may optionally be killed, such as by exposure of the organisms to a chemical fixative. The chemical fixative may also function as an extraction agent. One preferred chemical fixative is formaldehyde which, for example when used to kill MAP organisms, maintains the ability of surface antibody binding sites of MAP to bind with antibodies in serum from animals infected with the organism. A preferred concentration of formaldehyde is about 1% to 10% v/v, with a concentration of about 2% most preferred. Other chemical fixatives that may be used to kill infective organisms for use in the method of the invention include non-coagulant fixatives such as acetone, glyceraldehydes, glutaraldehyde, and paraformaldehyde, and less preferred coagulant fixatives such as ethanol and mercuric chloride.

Following the exposure of the test sample to the population of free surface antigens, it is then determined if antibodies from the test sample have bound to the antigens. Such determination typically is by the detection of conjugates of antibodies from the test sample and free surface antigens. Any method that is suitable to detect the presence of antibody binding to an antigen is suitable for the method of the invention.

In one preferred embodiment, antibody-free surface antigen binding is determined by flow cytometry. Such flow cytometry determination may be performed by analysis of a sample obtained by mixing a suspension containing a serum sample and a population of free surface antigens that are preferably bound to surfaces within a fluid, such as glass or plastic beads. A labeled anti-antibody, typically a fluorescein-labeled anti-antibody may be useful in determining binding in this way.

In another preferred embodiment, antibody-free surface antigen binding is determined by blot analysis, such as dot blot or Western blot analysis. Such dot blot determination may be performed by mixing a suspension containing a serum sample and a population of free surface antigens with an anti-antibody which is labeled, such as with biotin or colloidal gold, spotting this mixture on a membrane, such as a nitrocellulose or polyvinylidene fluoride (PVDF) membrane, and determining the presence of labeled free surface antigen-antibody conjugates fixed on the membrane. As detailed below, the diagnosis of infection with such methods is accurate, sensitive, and specific. Determination of infection with methods such as dot blot analysis permits diagnosis to be made by visual inspection and such methods are therefore capable of being performed by individuals who are not technically trained in sophisticated laboratory techniques.

Another means of determination of antibody-free surface antigen binding is an ELISA-like method whereby free surface antigens are immobilized on the surface of one or more wells and the degree of binding of antibodies in a test sample is determined by measurements of optical density. Another means is by a dipstick test such as is commonly used in determining pregnancy in women. Free surface antigens are immobilized on a test surface, such as on a strip of paper or nitrocellulose, and are brought into contact with antibodies in a sample fluid by dipping the surface on which the antigens are immobilized into the fluid. In the dipstick test, typically a colorimetric marker is utilized so that binding is determined by a visible color change on the test surface.

In another embodiment, the invention is a method for preparing a solid surface to which is adhered free surface antigens of an organism, such as a microorganism. The solid surface may be used to determine the presence in a test sample of antibodies that bind to the free surface antigens and, thereby, to diagnose infection of an animal due to the organism.

In accordance with this embodiment of the invention, free surface antigens of an organism are obtained by gentle dislodgement from the organism as described above. In this way, antigens that are collected from the organism are substantially only those that previously were found on the surface of the antigen and no, or substantially no, internal antigens of the organism are collected. If desired, free surface antigens obtained by gentle dislodgement of a multiplicity of organisms may be utilized.

The free surface antigens are immobilized onto a solid surface. If desired a coating buffer may be used to increase adherence of the antigens to the surface.

The solid surface may be an impermeable surface such as glass or plastic, such as is utilized in a well-plate, a slide, a petri dish, or a bead. Alternatively, the solid surface may be a permeable surface such as a paper or nitrocellulose.

In another embodiment, the invention is a solid surface to which are adhered free surface antigens of an organism, such as a microorganism. Preferably, a multiplicity of different free surface antigens is adhered to the solid surface. Preferably, the solid surface is free of antigens other than surface antigens of the organism. In a most preferred embodiment, the free surface antigens of a organism that are immobilized on the surface are obtained by gentle dislodgement as described above.

If desired, a multiplicity of different free surface antigens from a multiplicity of different organisms, such as microorganisms, is adhered to the solid surface. In this manner, the solid surface may be utilized for screening for the presence of infection due to an array of organisms.

The invention is further illustrated in the following non-limiting examples. The examples utilize samples of *Mycobacterium*, specifically *Mycobacterium avium*, and most specifically *Mycobacterium avium* subsp. *paratuberculosis* (also known as *Mycobacterium paratuberculosis*), referred to herein as MAP. This bacterium was selected as an example to illustrate the invention because infection with MAP, including in individuals suffering from Johne's disease in cattle and Crohn's disease in humans, are difficult to diagnose by conventional methods because the organism if frequently absent from samples obtained from infected subjects.

Thus, because the infection is a general process that is applicable to any microorganism from which surface antigens may be obtained without disruption of the microorganism with consequent obtaining of internal antigens together with surface antigens, the detection of infection due to MAP is a difficult test that illustrates the broad applicability of the invention.

EXAMPLE 1

Preparation of Immobilized Free Surface Antigens

Immobilized free surface antigens of *Mycobacterium avium* subsp. *paratuberculosis* (MAP, Linda strain) were prepared as follows. Six milligrams of the bacteria were harvested from 900 µl of bacterial culture by centrifugation at 2200 xg. The bacteria were mixed with 300 µl of an extraction agent selected from distilled water, methanol, ethanol, propanol, acetonitrile, acetone, chloroform, methylene chloride, ether, and hexane. The mixtures were then resuspended by vortexing for 1 min, centrifuged to form a pellet, and 50 µl of the supernatant was added to each well of a plastic 96-well plate. The plates were allowed to dry at room temperature causing the materials (free surface antigens) to adhere to the well surface.

EXAMPLE 2

Binding to Free Surface Antigens Extracted with Various Solvents

The wells prepared as described in Example 1 were washed with 100 µl of buffer A (phosphate buffered saline (PBS) containing 20% Superblock (Pierce Biotechnology, Inc., Rockford, Ill., USA) and 0.05% Tween 80), incubated for one hour at room temperature with 1:50 diluted serum from cows known to have or known not to have Johne's disease. After washing four times with 100 µl of PBS containing 0.5% Tween 20, the wells were incubated with biotinylated anti-bovine IgG polyclonal antibody (1:500 dilution in buffer A, Jackson ImmunoResearch Laboratories, Inc., West Grove, Pa., USA) for one hour at room temperature. After washing four times with 100 µl of PBS containing 0.5% Tween 20, the wells were then incubated with streptoavidin conjugated with horseradish peroxidase (1:1000 dilution in buffer A) for 1 hour at room temperature. After washing four times with 100 µl of PBS containing 0.5% Tween 20, bound antibodies were quantified by optical density with a microplate reader (Bio-Rad Laboratories, Hercules, Calif., USA) set at 415 nm. The results are shown graphically in FIG. 1.

As shown in FIG. 1, the method of the invention utilizing any of the extraction agents was able to detect the presence of MAP specific antibodies in the serum samples and that antibody binding was markedly higher in MAP positive serum samples than in MAP negative serum samples. This result establishes that each of the extraction agents was able to extract free surface antigens from the MAP organisms. As shown, the alcohols (methanol, ethanol, and propanol) extracted the greatest amount of MAP specific antigens.

EXAMPLE 3

Differential Binding with Various Concentrations of Ethanol

Free surface antigens of MAP and of *Mycobacterium avium* subsp. *avium* (MAA) were prepared as described in Example 1 using various concentrations of ethanol as the extraction agent. Binding of antibodies in serum from animals known to have Johne's disease was determined as described in Example 2 for each of the various concentrations using either MAA or MAP free surface antigens. The results are shown in FIG. 2.

Figure 2:
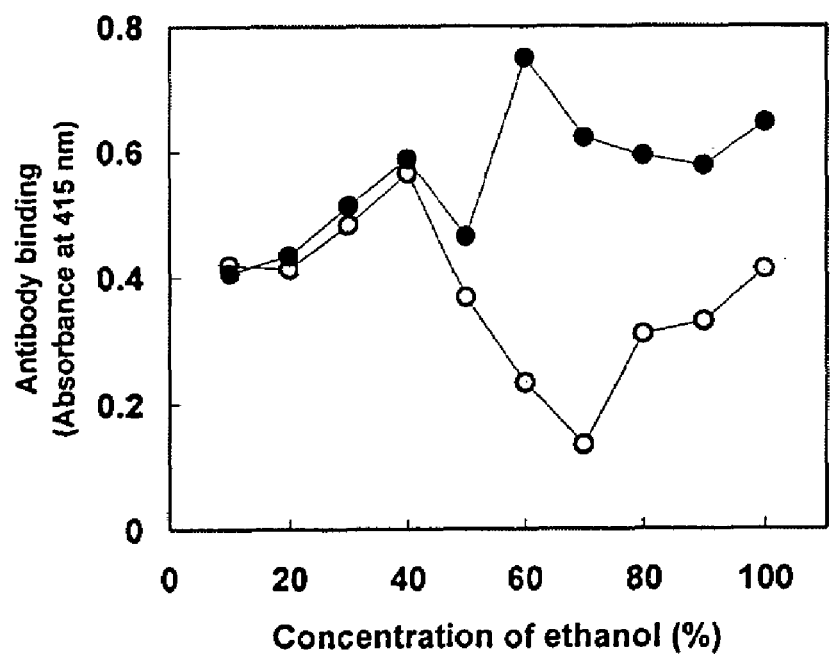
FIG. 2 is a graph showing the relative ability of extracts of MAP and MAA obtained according to the invention with treatment using varying concentrations of ethanol to bind to antibodies in serum from animals known to be infected with MAP. Solid circles represent ethanol extracts of MAP. Open circles represent ethanol extracts of MAA.

As shown in FIG. 2, wells containing antigen that was extracted at concentrations of ethanol below 40% showed similar levels of antibody binding when contacted to Johne's disease positive serum using extracts of either MAA or MAP. At a concentration of ethanol of 50% and higher, increased antibody binding was observed with MAP extracts compared to that with MAA extracts. The most significant differences in antibody binding between MAP and MAA extracts were observed at concentrations of ethanol higher than 60%, and especially between 60% and 70%.

EXAMPLE 4

Specificity

Serum samples from cows known to be infected with MAP and cows known to be uninfected with MAP were analyzed as described in the above examples using MAA and MAP extracts, respectively, that were obtained using ethanol at a concentration of 70%. The results are shown graphically in FIG. 3.

Figure 3:
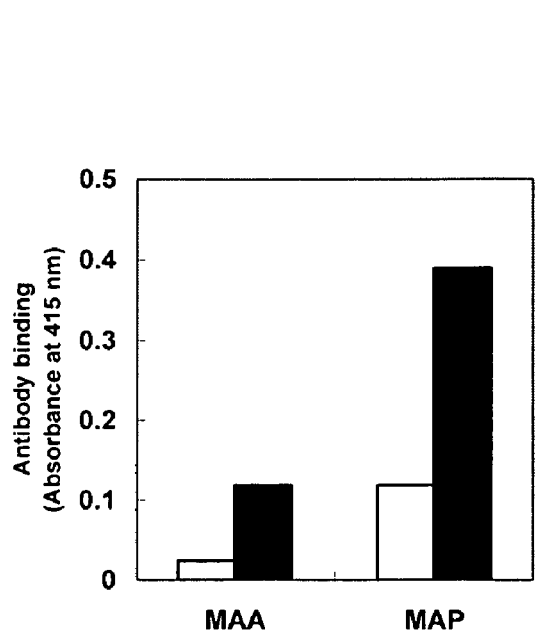
FIG. 3 is a bar graph comparing antibody binding to extracts of MAP and MAA obtained according to the invention with using 70% ethanol in animals known to be infected with MAP and animals known to be not infected with MAP. Solid bars represent MAP-infected cattle. Open bars represent MAP-noninfected cattle. In both infected and noninfected cattle, antibody binding to MAP extracts was noticeably much higher than to MAA extracts.

As shown in FIG. 3, the method of the invention correctly identified infection with MAP in the samples and showed a lack of false positive diagnoses as the method of the invention did not show binding when extracts of MAA were used as the test antigen. This study establishes the high specificity of the method of the invention, which is capable of distinguishing between very closely related organisms, even between MAP and MAA which are currently classified as subspecies of the same bacterial species.

EXAMPLE 5

Preparation of Immobilized Free Surface Antigens

Five hundred micrograms of MAP were suspended in various concentrations of formaldehyde solution containing 10% methanol for 20 min at room temperature. The suspension was sonicated for 2 seconds, centrifuged at 2200 xg, and the supernatant was used as antigen as in Example 1. Fifty µl of the supernatant was added to each well of a plastic 96-well plate. The plates were allowed to dry at room temperature causing the materials (free surface antigens) to become immobilized to the well surface.

EXAMPLE 6

Binding to Free Surface Antigens Extracted with Varying Concentrations of Formaldehyde The wells prepared as described in Example 5 were washed with 100 µl of buffer A (phosphate buffer saline (PBS) containing 20% Superblock (Pierce Biotechnology, Inc., Rockford, Ill., USA) and 0.05% Tween 80), incubated for one hour at room temperature with 1:50 diluted serum from cows known to have or known not to have Johne's disease. After washing four times with 100 µl of PBS containing 0.5% Tween 20, the wells were incubated with biotinylated anti-bovine IgG polyclonal antibody (1:500 dilution in buffer A, Jackson ImmunoResearch Laboratories, Inc., West Grove, Pa., USA) for one hour at room temperature. After washing four times with 100 µl of PBS containing 0.5% Tween 20, the wells were then incubated with streptoavidin conjugated with horseradish peroxidase (1:1000 dilution in buffer A) for 1 hour at room temperature. After washing four times with 100 µl of PBS containing 0.5% Tween 20, bound antibodies were quantified by optical density with a microplate reader (Bio-Rad Laboratories, Hercules, Calif., USA) set at 415 nm. The results are shown graphically in FIG. 4.

Figure 4:
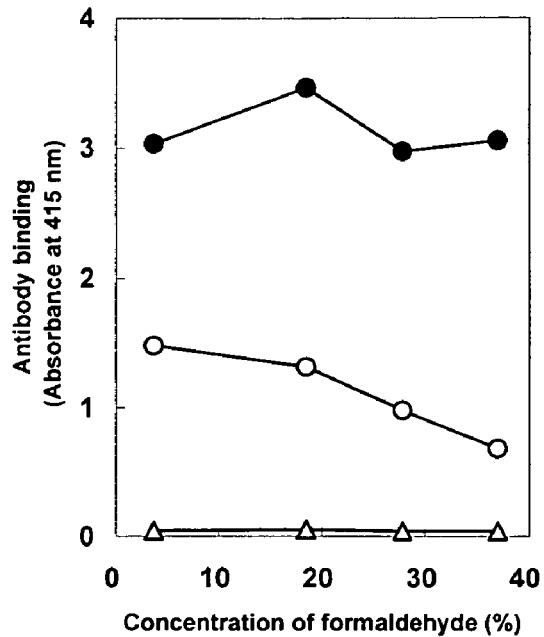
FIG. 4 is a graph showing the effects of using various concentrations of formaldehyde as an extraction agent on antibody binding in sera from MAP positive and MAP negative cattle. Solid circles represent serum from MAP positive animals. Open circles represent serum from MAP negative animals. Open triangles represent dilution buffer and no serum.

As shown in FIG. 4, wells containing MAP antigen that was extracted at various concentrations of formaldehyde showed similar levels of antibody binding when contacted to Johne's disease positive serum. However, levels of antibody binding in sera from Johne's disease negative cows decreased as the concentration of formaldehyde was increased. The data of FIG. 4 indicates that higher levels of specificity are obtained for diagnosis of MAP infection when utilizing higher concentrations of formaldehyde as the extracting agent, up to full strength of formaldehyde of 37%.

EXAMPLE 7

Binding to Free Surface Antigens Extracted with Varying Duration of Sonication

Wells were prepared as described in Example 6 using 37% formaldehyde with 10% methanol as the extraction agent and with varying durations of sonication. The results are shown graphically in FIG. 5.

Figure 5:
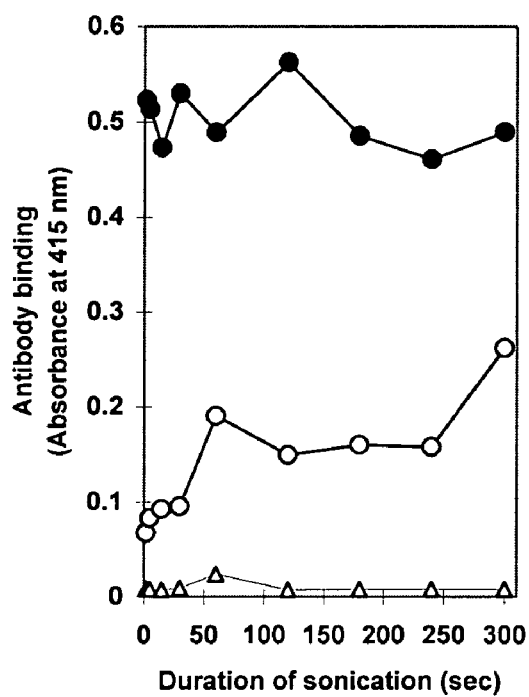
FIG. 5 is a graph showing the effects of using different durations of sonication when extracting surface antigens from MAP on antibody binding in sera from MAP positive and MAP negative cattle. Solid circles represent serum from MAP positive animals. Open circles represent serum from MAP negative animals. Open triangles represent dilution buffer and no serum.

As shown in FIG. 5, virtually any amount of sonication is sufficient to detect binding of antibodies from MAP infected animals, indicating that, based on this one measurement, sensitivity of the diagnostic capability of the invention does not appear to change as a function of time of sonication. In contrast, increasing the time of sonication resulted in increased antibody binding seen in serum from MAP uninfected animals, indicating that specificity of the diagnostic method decreases as a function of increased sonication time. It is conceived that the decrease in specificity of the method of the invention with increases in time of sonication is due to release of internal antigens of MAP, among which are antigens that are not specific to MAP.

EXAMPLE 8

Specificity and Sensitivity

Free surface antigens were extracted from MAP organisms and were immobilized onto wells as described in Examples 5 and 6. Formaldehyde at a concentration of 37% with 10% methanol was used as the extraction agent and sonication was applied in a burst of about 2 seconds.

Two populations of cattle were tested to determine the sensitivity and specificity of the method of the invention. Serum samples from 35 Johne's disease-negative cattle and from 23 Johne's disease-positive cattle were tested. An S/P value of 0.3 was established as a cutoff to determine a positive diagnosis using the following formula: S/P value=(S−NC)/(S−PC), where S is optical density (absorbance at 415 nm) of a control sample, NC is optical density obtained using serum from negative cattle, and PC is optical density using serum from positive cattle. Results are shown in FIG. 6.

Figure 6:
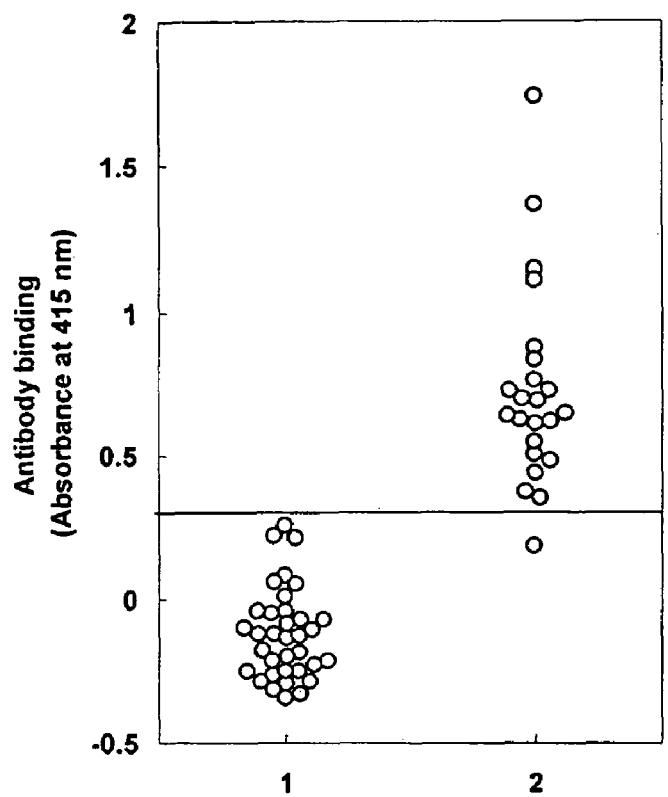
FIG. 6 is a graph showing the ability of the method of the invention to detect MAP infection in two populations of Johne's disease negative and Johne's disease positive cattle. An S/P value of 0.3 was used as a cutoff wherein antibody binding above this level was determined to be a positive diagnosis and below this level was determined to be a negative diagnosis. Serum samples in column 1 were from Johne's disease negative cattle. Serum samples in column 2 were from Johne's disease positive cattle.

As shown in FIG. 6, every one of the 35 negative cattle tested negative by the diagnostic method of the invention, providing a specificity for the test at an S/P value of 0.3 of 100%. Of the 23 positive cattle, 22 tested positive by the diagnostic method of the invention, providing a sensitivity for the test at this S/P value of 95.6%. FIG. 6 further shows that, if a lower S/P value is used, for example 25% which is used in the commercial Johne's ELISA test, the sensitivity of the test of the invention would be measured at 100%, although the specificity would fall to 94.3%. The results clearly show the extremely high combination of specificity and sensitivity obtainable by the diagnostic method of the invention.

EXAMPLE 9

Diagnosis in Bodily Fluids Other Than Blood

Free surface antigens were obtained from MAP organisms and immobilized into wells as described above in Example 8. Serum samples and milk samples from 20 cows, some of which were MAP positive and some of which were MAP negative were tested according to the invention. Results are shown in FIG. 7.

Figure 7:
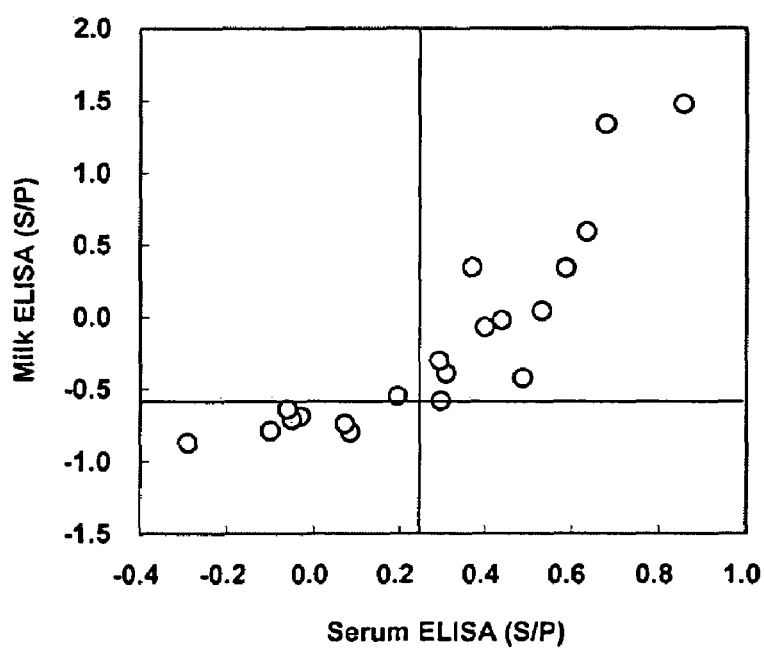
FIG. 7 is a graph of S/P values obtained on paired milk and serum samples from individual cows, some of which were infected with MAP and others of which were not infected with MAP. For serum, an S/P value of 0.25 was determined to be a cutoff, and for milk, and S/P value of −0.6 was determined to be a cutoff. On the graph, reactions (open circles) below the horizontal (X-axis) S/P value of 0.25 and to the left of the vertical (Y-axis) S/P value of −0.6 are negative.

As shown in FIG. 7, 12 of the 20 cows tested MAP infection positive by diagnostic testing of serum. Of the 12 serum positive cows, every one tested positive by diagnostic testing of milk. In addition, 8 of the 20 cows tested MAP negative by diagnostic testing of serum. Of these 8 serum negative cows, 7 tested negative by diagnostic testing of milk. Only one cow showed a discrepancy between the testing on serum and on milk, and that cow, which tested negative on serum, had only a borderline positive test when performed on milk.

EXAMPLE 10

Comparison Testing

One hundred and five (105) cows were divided into three groups based on two criteria, (1) results of fecal culture test for MAP and (2) development of symptoms of Johne's disease. Group I contained 30 cows which were diagnosed negative for MAP by fecal culture test and showed no signs of Johne's disease. To confirm the negative status of this group, each cow was also tested for MAP infection by convention ELISA testing and tests for gamma interferon with negative results. Group II contained 52 cows which tested negative by fecal culture and conventional ELISA, but which developed signs of Johne's disease. Thus, in these cows, the fecal culture and conventional ELISA results were false negative test results. Group III contained 23 cows which tested positive by fecal culture for the presence of MAP. Fecal culture was performed several times on each cow, generally four times, before fecal culture was determined to be negative. For example, of the 23 Group III cows, 9 had at least one negative fecal culture test but tested positive on at least one other test.

Serum samples were obtained from each of the 105 cows and were tested for the presence of antibodies against MAP in two ways. The serum was tested by mixing a sample with a population of intact MAP organisms and detecting antibody/MAP binding by flow cytometry. This method is disclosed in Eda, U.S. patent application Ser. No. 10/832,761, filed Apr. 27, 2004, and was shown to be a method that is more sensitive and more specific in diagnosing a microbial infection than is conventional ELISA testing. An S/P value of 0.23 or greater was determined to be a positive test by the flow cytometry method. The serum was also tested by the method of the present invention as described in the above examples. The MAP free surface antigens were obtained by gentle dislodgment by short burst sonication of an MAP suspension in 37% formaldehyde and 10% methanol. An S/P value of 0.35 or greater was determined to be a positive test by this method. Results of the testing are shown below in Table 1.

TABLE 1

| COW GROUP | FECAL CULTURE | | INTACT MAP | | MAP SURFACE ANTIGENS | |
|---|---|---|---|---|---|---|
| | Positive | Negative | Positive | Negative | Positive | Negative |
| Group I (n = 30) | 0 | 30 | 1 | 29 | 3 | 27 |
| Group II (n = 52) | 0 | 52 | 37 | 15 | 50 | 2 |
| Group III (n = 23) | 23 | 0 | 20 | 3 | 22 | 1 |

As shown in Table 1, of the 30 Group I cows, which tested 100% negative by fecal culture, one of these was found by the "Intact MAP" test of the previously filed patent application to be positive. However, the MAP Surface Antigens test of the present invention determined that 3 of the Group I cows, including the one found to be positive by Intact MAP test, were positive for infection with MAP.

Table 1 further shows that, of the 52 Group II cows, those having false negative fecal culture and conventional ELISA tests, the Intact MAP test correctly diagnosed 37 of these 52 cows (71%) to be positive. This shows the remarkable improvement in diagnosis that is attainable with the Intact MAP test compared to presently available diagnostic methods. However, the MAP Surface Antigens test of the present invention provided an even more accurate diagnosis. This test correctly diagnosed 50 of these 52 cows (96%) to be positive. These results establish the extremely high sensitivity of the method of the invention, even higher than that of the Intact MAP test which itself has a higher sensitivity than do presently available diagnostic methods.

The data in Table 1 shows that 23 Group III cows were diagnosed positive by fecal culture test. Of these 3 (13%) tested negative by the Intact MAP test and 1 (4.3%) tested negative by the MAP Surface Antigens test. At first assessment, this data might suggest that the fecal culture test is more sensitive than either of the other two tests. However, when data on the testing of each individual cow is examined, it is clear that the specificity of both the Intact MAP test and the MAP Surface Antigen test of the present invention are markedly higher than that of the fecal culture test.

The data on individual cow testing, which is not shown in Table 1, is shown in FIG. 8. FIG. 8 shows that the fecal culture test was performed 4 times on 14 of the Group III cows, 3 times on 5 of the Group III cows, and two times on one of the Group III cows, for a total of 88 fecal culture tests performed. Of these tests, 21 were negative. Therefore, the sensitivity of the fecal culture test is calculated to be 76% (67/88). In contrast, the sensitivity of the Intact MAP test (20/23) was 87% and that of the MAP Surface Antigens test of the invention (22/23) was 95.7%. Thus, the data establishes the high sensitivity of the test of the present invention. herein will be apparent to those skilled in the art. It is intended that such modifications be encompassed in the claims that follow.

The invention claimed is:

1. A method for diagnosing the presence in an animal of an infection caused by a particular organism comprising obtaining a test sample from the animal, exposing the test sample to a multiplicity of free surface antigens of the organism that have been obtained by removing the antigens from the surface of the organism without disrupting the organism and removing internal antigens from the organism, permitting an antibody in the test sample that binds to an antibody binding site on a surface antigen of the organism to bind to the antibody binding site, and determining if the test sample contains an antibody that binds to the free surface antigens of the organism by detecting the presence of one or more antibodies in the test sample that are bound to the free surface antigens, thereby diagnosing the presence of an infection in the animal due to the particular organism, wherein the organism is one that is capable of eliciting an antibody response in an animal infected thereby and wherein surface antigens may be obtained from the organism by gentle dislodgment.

2. The method of claim 1 wherein the organism is a microorganism.

3. The method of claim 2 wherein the microorganism is a bacterium.

4. The method of claim 3 wherein the gram-positive bacterium is a *mycobacterium*.

5. The method of claim 4 wherein the *mycobacterium* is *Mycobacterium avium* subsp. *paratuberculosis*.

6. The method of claim 1 wherein the removal of the antigens from the surface of the organism is by mechanical treatment of the organism combined with treatment of the organism with an extraction agent, and isolating the antigens from the extraction agent.

7. The method of claim 1 wherein the fluid is blood, serum, or plasma.

8. The method of claim 6 wherein the mechanical treatment is sonication or vortexing.

9. The method of claim 1 wherein the exposing of the test sample to the free surface antigens is by mixing the test sample and the free surface antigens in a vessel.

10. The method of claim 9 wherein the detection of binding is by flow cytometry.

11. The method of claim 9 wherein the detection of binding is by blot analysis.

12. The method of claim 1 wherein the exposing of the test sample to the free surface antigens is on a surface.

13. The method of claim 12 wherein the free surface antigens are immobilized on the surface of one or more wells and the binding of antibodies in the test sample to the free surface antigens is determined by measurements of optical density.

14. The method of claim 12 wherein the free surface antigens are immobilized on a test surface and are exposed to the test sample by dipping the surface on which the antigens are immobilized into a fluid test sample.

15. The method of claim 14 where a colorimetric marker is utilized so that binding is determined by a visible color change on the test surface.

16. The method of claim 1 wherein the removal of the antigens is by agitation of the organism which is suspended in a fluid containing an extracting agent.

17. The method of claim 16 wherein the agitation is by sonication or vortexing.

18. The method of claim 16 wherein the extraction fluid is selected from the group consisting of distilled water, an alcohol, acetonitrile, acetone, chloroform, methylene chloride, ether, and hexane.

19. The method of claim 16 wherein the extraction fluid is an alcohol selected from the group consisting of methanol, ethanol, and propanol.

20. The method of claim 3 wherein the bacterium is gram-positive.

21. A method for diagnosing the presence in an animal of an infection caused by a particular organism comprising obtaining a test sample from the animal, exposing the test sample to a multiplicity of non-proteinaceous free surface antigens of the organism that have been obtained by gentle dislodgment from the organism, permitting an antibody in the test sample that binds to an antibody binding site on the free surface antigens to bind to the antibody binding site, and determining if the test sample contains an antibody that binds to the free surface antigens of the organism by detecting the presence of one or more antibodies in the test sample that are bound to the free surface antigens, thereby diagnosing the presence of an infection in the animal due to the particular organism, wherein the organism is one that is capable of eliciting an antibody response in an animal infected thereby and wherein non-proteinaceous surface antigens may be obtained from the organism by gentle dislodgment.

22. A method for diagnosing the presence in an animal of an infection caused by a particular organism comprising obtaining a test sample from the animal, exposing the test sample to a multiplicity of carbohydrate free surface antigens of the organism that have been obtained by gentle dislodgment from the organism, permitting an antibody in the test sample that binds to an antibody binding site on the free surface antigens to bind to the antibody binding site, and determining if the test sample contains an antibody that binds to the free surface antigens of the organism by detecting the presence of one or more antibodies in the test sample that are bound to the free surface antigens, thereby diagnosing the presence of an infection in the animal due to the particular organism, wherein the organism is one that is capable of eliciting an antibody response in an animal infected thereby and wherein carbohydrate surface antigens may be obtained from the organism by gentle dislodgment.

* * * * *